United States Patent [19]

Cocuzza

[11] Patent Number: 4,908,453

[45] Date of Patent: Mar. 13, 1990

[54] REAGENTS FOR THE PREPARATION OF 5'-BIOTINYLATED OLIGONUCLEOTIDES

[75] Inventor: Anthony J. Cocuzza, Wilmington, Del.

[73] Assignee: E. I. Du Pont De Nemours and Company, Wilmington, Del.

[21] Appl. No.: 300,504

[22] Filed: Jan. 23, 1989

[51] Int. Cl.$^4$ ............................................. C07F 9/65
[52] U.S. Cl. .................................. 548/113; 540/450; 540/454; 540/455; 540/460; 540/461; 540/542; 544/50; 544/52; 544/54; 544/57; 544/90; 544/133; 544/150; 544/243; 544/244; 544/337; 546/21
[58] Field of Search ............... 540/450, 454, 455, 460, 540/461, 542; 544/50, 52, 54, 57, 90, 133, 150, 243, 244, 337; 546/21; 548/113

[56] References Cited

U.S. PATENT DOCUMENTS 4,605,735  8/1986  Miyoshi et al. ..................... 536/27
4,711,955  12/1987  Ward et al. ......................... 536/29

FOREIGN PATENT DOCUMENTS 202758  11/1986  European Pat. Off. .
305201  3/1989   European Pat. Off. .

OTHER PUBLICATIONS

Alves et al., Tetrahedron Letters, vol. 30, No. 23 (1989), pp. 3089–3092.
Chollet et al., Nucleic Acids Res. 13, 1529–1541 (1985).
Wachter et al., Nucleic Acids Res. 14, 7985–7994 (1986).
Agrawal et al., Nucleic Acids Res. 14, 6227–6245 (1986).
Urdea et al., Nucleic Acids Res. 16, 4937–4956 (1980).
Cook et al., Nucleic Acids Res. 16, 4077–4095 (1980).
Kempe et al., Nucleic Acids Res. 13, 45–57 (1985).

Primary Examiner—Richard L. Raymond

[57] ABSTRACT

Reagents useful in the preparation of 5'-biotinylated oligonucleotides are disclosed.

20 Claims, No Drawings

REAGENTS FOR THE PREPARATION OF 5'-BIOTINYLATED OLIGONUCLEOTIDES

BACKGROUND OF THE INVENTION

1. Field of the Invention

This invention relates to reagents useful in the preparation of 5'-biotinylated oligonucleotides.

2. Summary of the Background

Oligonucleotides and single-stranded DNA bearing reporter groups are generally referred to as nucleic acid probes. Nucleic acid probes can be used to detect nucleotide sequences of interest in DNA or RNA by specific hybridization and have proved extremely valuable for a variety of uses, including gene localization and the detection of mutations. Such probes are therefore useful as diagnostic tools for both research and clinical purposes. The detection of nucleic acid sequences by nucleic acid probes can be carried out using standard methods, such as "Southern Hybridization," "Sandwich Hybridization," "In situ Hybridization," or the "Dot Blot" technique.

Although high specific activity $^{32}P$ has commonly been used as the reporter group for nucleic acid probes, the use of this radioisotope is problematic from both a logistical and a health standpoint. The short half-life of $^{32}P$ necessitates the anticipation of reagent requirements several days in advance and prompt use of such a reagent. Once $^{32}P$-tagged nucleic acid probes have been generated, they are prone to self-destruction and must be immediately used in hybridization assays. Subsequent autoradiography required for visualization of the labeled probes is a slow process (overnight exposures are common). Finally, possible health risks are associated with the use and disposal of such potent radioisotopes. To address these problems, replacement of $^{32}P$/autoradiography with alternative, nonradioisotopic reporter/detection systems has been considered.

The most common nonradioisotopic reporter group used in nucleic acid probes is (+)-biotin (vitamin H). This is due in particular to its safety and the sensitivity of the systems developed for its detection. (+)-Biotin forms very tight ($K_D = 10^{-15}M$) complexes with the proteins avidin and streptavidin, which can be easily visualized by enzyme-based systems, many of which are commercially available. All such systems are based on avidin or streptavidin chemically bound to an enzyme that catalyzes a reaction generating an easily detectable substance. Preferred enzymes include alkaline phosphatase, beta galactosidase, horseradish peroxidase, and luciferase. These enzyme systems produce substances that are easily detected by their color, fluorescence, or luminescence. (+)-Biotin is [3aS-(3a$\alpha$,4$\beta$, 6a$\alpha$)]-hexahydro-2-oxo-1H-thieno[3,4-d]-imidazole-4-pentanoic acid; however, it is the hexahydro-2-oxo1H-thieno[3,4-d]-imidazole portion of the molecule that is responsible for its binding to avidin and streptavidin. Hereafter, "biotinylated" substances and substances containing the "biotin group" refer to substances containing hexahydro-2-oxo-1H-thieno[3,4-d]-imidazole.

Biotinylated nucleic acid probes can either be long (generally >100 nucleotides) or short (generally 8-30 nucleotides) in length, and both types have particular uses and advantages. Long biotinylated nucleic acid probes have been prepared by the multiple incorporation of biotinylated nucleoside triphosphates by nick translation using a DNA polymerase or by 3'-tailing with multiple biotinylated nucleosides using terminal deoxynucleotide transferase, see Ward, et al., U.S. Pat. No. 4,711,955. Drawbacks to these enzymatic methods for preparing biotinylated probes include the expense of biotinylated nucleoside triphosphates and the need for obtaining the probe's sequence from a natural source.

Short nucleic acid probes ("oligonucleotide probes") have two major advantages over long probes. First, they are much more sensitive to small numbers of base mismatches with their complementary target DNA, making them particularly useful, for example, in detecting mutations. Second, although short probes cannot be easily synthesized enzymatically, they can be conveniently prepared in large quantities (10-100 nanomoles) by introducing a reporter group onto readily available synthetic oligonucleotides. For example, short radioactive probes are most typically prepared by enzymatically labeling synthetic oligonucleotides with $^{32}P$.

The preferred method of synthesizing oligonucleotides is by solid phase synthesis using either the phosphotriester, phosphoramidite, or hydrogen phosphonate approach. Most oligonucleotides are now prepared very conveniently by commercially available automated DNA synthesizers, all of which use the phosphoramidite approach or, more recently, the H-phosphonate approach.

A number of methods have been described for the preparation of synthetic biotinylated oligonucleotide probes. In one general approach, an oligonucleotide possessing an added group with unusual reactivity, for example, an aliphatic amino group, is first prepared either by solid phase synthesis or by a combination of solid phase and solution techniques. The purified oligonucleotide possessing the unusually reactive group is treated with a reactive derivative of (+)-biotin to afford the biotinylated probe, which is then further purified. Examples of this and related approaches have been disclosed by Chollet, et al., Nucleic Acids Res. 13, 1529-41 (1985); Wachter, et al., Nucleic Acids Res. 14, 7985-94 (1986); Agrawal, et al., Nucleic Acids Res. 14, 6227-45 (1986); Urdea, et al., Nucleic Acids Res. 16, 4937-56 (1988); and Cook, et al., Nucleic Acids Res. 16, 4077-95 (1980). All of these approaches to biotinylated oligonucleotide probes require specialized reagents, as well as considerably more time, effort, and chemical expertise than does automated chemical synthesis.

There are two examples of methods for preparing biotinylated oligonucleotide probes in which all reactions, including the final biotin attachment step, are performed on a solid support. Carr, et al., European Patent Application No. 86302750.4 (publ. 1986) have disclosed a method for preparing 5'-biotinylated oligonucleotides by reacting the deblocked 5'-hydroxy group of a solid supported oligonucleotide with a phosphorylated derivative of (+)-biotin in the presence of a condensing reagent. Kempe, et al., Nucleic Acids Res. 13, 45-57 (1985) have described a similar approach in which the deblocked 5'-hydroxy group of a solid supported oligonucleotide is first treated with p-chlorophenyl-phosphoditriazolide, the remaining phosphoroustriazole bond is hydrolyzed, and finally the phosphorylated oligonucleotide is treated with 2-(biotinylamido)ethanol in the presence of a condensing reagent. Although these two approaches have the general advantages of solid phase synthesis, they require reagents, solvents, and reaction conditions that are not commonly used in commercial automated DNA synthesizers. Consequently, solid supported oligonucleotide probes prepared using these methods on an automated DNA synthesizer must be biotinylated manually.

The purpose of the present invention is to overcome the disadvantages encountered in the prior art by providing biotinylating reagents useful for directly preparing 5'-biotinylated oligonucleotides. The reagents of the present invention make 5'-biotinylated oligonucleotides as accessible as ordinary oligonucleotides and are compatible with automated DNA synthesizers that utilize phosphoramidite chemistry.

SUMMARY OF THE INVENTION

The present invention provides chemical reagents of the formula

Bt-(SG)-A-Q wherein Bt is

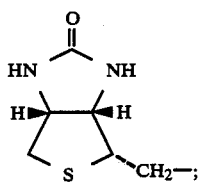

SG is an organic diradical spacer group that separates Bt from A at a distance sufficient to allow efficient complexation of Bt to avidin or streptavidin;

A is selected from the group consisting of -O-, -S-, $$-\overset{|}{N}R, \text{ and } -\overset{|}{C}RR^1,$$

wherein R and $R^1$ are independently selected from the group consisting of H, $C_{3-10}$ branched alkyl, $C_{1-10}$ unbranched alkyl, $C_{6-10}$ aryl, $C_{7-12}$ alkaryl, and $C_{7-12}$ aralkyl;

Q is selected from the group consisting of

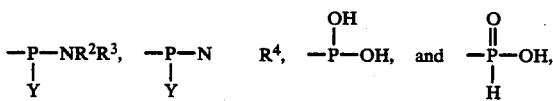

(1)   (2)   (3)   (4)

and salts thereof; wherein $R^2$ and $R^3$ are independently selected from the group consisting of $C_{3-10}$ branched alkyl and $C_{1-12}$ unbranched alkyl; $R^4$ is selected from the group consisting of $-(CRR^1)_m(A)_n(CRR^1)m-$,

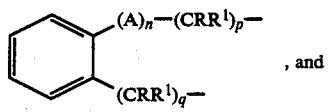

, and

R, $R^1$ and A are as defined above; m=1-6; n=0-1; p=1-10; q=0-10, provided that 2m+n ≦12, and further provided that 2≦n+p+q≦13; and Y is any phosphate-protecting group.

DETAILED DESCRIPTION OF THE INVENTION

The present invention provides chemical reagents of the formula

Bt-(SG)-A-Q wherein
Bt is

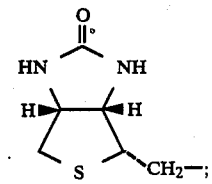

SG is an organic diradical spacer group that separates Bt from A at a distance sufficient to allow efficient complexation of Bt to avidin or streptavidin;

A is selected from the group consisting of -O-, -S-, $$-\overset{|}{N}R, \text{ and } -\overset{|}{C}RR^1,$$

wherein R and $R^1$ are independently selected from the group consisting of H, $C_{3-10}$ branched alkyl, $C_{1-10}$ unbranched alkyl, $C_{6-10}$ aryl, $C_{7-12}$ alkaryl, and $C_{7-12}$ aralkyl;

Q Is selected from the group consisting of

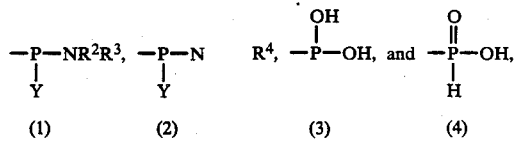

(1)   (2)   (3)   (4)

and salts thereof; wherein $R^2$ and $R^3$ are independently selected from the group consisting of $C_{3-1}$ branched alkyl and $C_{1-12}$ unbranched alkyl; $R^4$ is selected from the group consisting of $-(CRR^1)_m(A)_n(CRR^1)m-$,

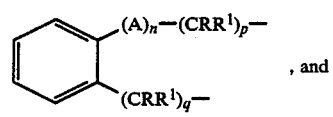

, and

R, $R^1$ and A are as defined above; m=1-6; n=0-1; p=1-10; q=0-10, provided that 2m+n ≦12, and further provided that 2≦n+p+q ≦13; and Y is any phosphate-protecting group.

In a preferred embodiment, SG is $-(CH_2)_r-X-$; r =2-3; X is selected from the group consisting of $-CH_2-$, $-X^1L-$, and

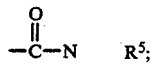

$X^1$ is selected from the group consisting of $-CH_2O-$, $-CH_2S-$,

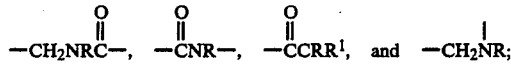

R and $R^1$ are as defined above; and $R^5$ is selected from are as defined above; and R the group consisting of

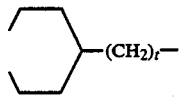

and alkyl-substituted derivatives thereof; $t=0-10$; and L is selected from the group consisting of substituted and unsubstituted derivatives selected from the group consisting of $C_{2-20}$ alkylene wherein the alkylene segment may contain one or more groups selected from the group consisting of arylene, cycloalkylene, heterocyclene, ether, thioether, sulfone, sulfoxide, amide, ureido, keto, and dithio; $C_{3-8}$ cycloalkylene; $C_{4-20}$ alkylenecycloalkyl; $C_{6-10}$ arylene;

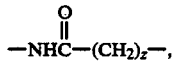

wherein $z=1-10$; $C_{7-20}$ arylalkylene; and 3-10 membered ring aromatic or alicyclic heterocyclenes wherein the heteroatom(s) may be selected from the group consisting of N, O and S. These heteroatom linkages must not be so proximate as to form a linkage that is unstable to the reactions involved in oligonucleotide synthesis. Moreover, ester or thioester groups should not be present in the backbone of X or L because these groups are likely to be cleaved during the ammonia treatment that is typically the final step of solid-state oligonucleotide synthesis.

Preferably, in the above embodiment, r is 2, X is $-CH_2-$, and A is $-CH_2-$. Additionally, a preferred group of compounds are those wherein r is 3, and more preferred compounds within this group include those wherein X is $-CH_2-$ and those wherein A is $-O-$.

When A is $-O-$, these reagents are commonly known (with reference to the activatable phosphorus group, Q) as phosphoramidites (structures 1 and 2 above), phosphorous acids (structure 3 above), and H-phosphonates (structure 4 above). Structures (3) and (4) represent moderately strong acids, and the reagents represented by these structures are generally isolated and used as their organically soluble salts. The H-phosphonate forms (4) of these reagents are generally in equilibrium with the phosphorous acid forms (3), with the H-phosphonates strongly favored. Analogous equilibria are possible when A is $-S-$,

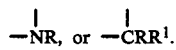

When A is $-O-$, preferred X values include $-CH_2-$ and

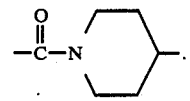

Additionally, a preferred embodiment is wherein X is $-X^1-L-$, $X^1$ is

and R is selected from the group consisting of H, $C_{1-4}$ unbranched alkyl, and $C_{3-5}$ branched alkyl, with most preferred values of R selected from the group consisting of H and $CH_3$.

Because current automated DNA synthesizers primarily use the phosphoramidite approach to oligonucleotide synthesis, the most preferred phosphorus reagents of this invention are phosphoramidites, i.e., when A is $-O-$ and the phosphorus group, Q, is selected from the group consisting of

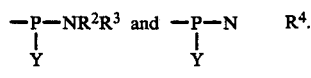

(1)              (2)

Phosphoramidite reagents can be synthesized from alcohols by a number of approaches known in the art. Examples 1-4 below describe the synthesis of phosphoramidite reagents by a modification of the method of Barone, et al., Nucleic Acids Res. 12, 4051 (1984).

Current DNA synthesizers are also compatible with the H-phosphonate approach to oligonucleotide synthesis, and the H-phosphonates and the tautomeric phosphorous acids, wherein A is $-O-$ and Q is selected from the group consisting of

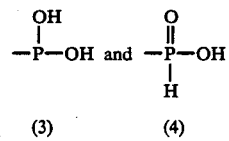

(3)              (4)

are also reagents of the present invention. H-phosphonates may be prepared from alcohols by a number of methods known in the art, such as those of Froehler, et al., Nucleic Acids Res. 14, 5399-5407 (1986) and Sinha, et al., Nucleic Acids Res. 16, 2659 (1988).

The phosphorus group, Q, includes Y, which can be any phosphate-protecting group. Preferred Y values are those selected from the group consisting of $4-Cl-C_6H_4-O-$; $2-Cl-C_6H_4-O-$; $4-NO_2-C_6H_4-O-$; $4-NO_2-C_6H_4CH_2-O-$; $2,4-NO_2-C_6H_3CH_2CH_2-O-$; $2,4-Cl_2-C_6H_3-O$; $2,3-Cl_2-C_6H_3-O-$; $NCCH_2CH_2O-$; $NCCH_2C(CH_3)_2-O-$; $CH_3O-$; $(Z)_3CCH_2-O-$; $(Z)_3CC(CH_3)_2-O-R'S-$; $R'SCH_2CH_2-O-$; $R'SO_2CH_2CH_2-O-$; and $R'NH-$, wherein Z is selected from the group consisting of Cl, Br, and I, and R' is selected from the group consisting of H, $C_{3-10}$ branched alkyl, $C_{1-10}$ unbranched alkyl, $C_{6-10}$ aryl, $C_{7-12}$ alkaryl, and $C_{7-10}$ aralkyl.

A most preferred embodiment is wherein Q is

(1)

and $R^2$ and $R^3$ are —CH(CH$_3$)$_2$. Additionally, the preferred Y groups for this combination are those selected from the group consisting of NCCH$_2$CH$_2$O and CH$_3$—. Specifically, preferred compounds within this group include those wherein R is H and L is $C_{2-20}$ alkylene, with L selected from the group consisting of (CH$_2$)$_2$ and (CH$_2$)$_3$ being most preferred; wherein R is H and L is 1,4-cyclohexylene; wherein R is H, L is

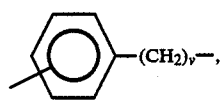

and v=1—10, with

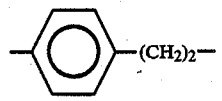

as the most preferred L; and wherein R is H, L is

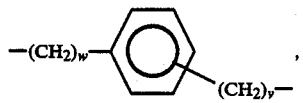

v is 1–10, and w is 1–10.

Using methods known in the art, a covalent link can be made between biotin or a derivative of biotin and the spacer group, SG, for example, using biotinal or biotin hydrazide. Then a covalent link can be made between the spacer group, SG, and the activatable phosphorus group, Q. For reasons of synthetic ease and stability, Q is usually attached to an oxygen that was formerly part of a hydroxyl group attached to the spacer group, SG. In some cases, the activatable phosphorus group, Q, can be attached directly to a derivative of biotin at a site that does not interfere with its utility as a reporter. In other cases, the covalent linkages can be formed by selectively attaching biotin or a derivative of biotin to one end of a difunctional molecule and the activatable phosphorus to the other end of this molecule.

For example, this can be accomplished by forming an amide bond between the biotin carboxyl group and the amino group of an amino alcohol. The hydroxyl group of the amino alcohol linker can then be used to form a covalent bond to the activatable phosphorous group. In some cases, it may be necessary to protect sensitive functional groups on the spacer group during the attachment of the activatable phosphorus group, activation of the phosphorus group, or attachment of the phosphorus group to the 5'-hydroxyl group of the oligonucleotide. The nature of the protecting group(s), if present, will depend on the sensitive functional groups on the biotin-linker group. Methods for protecting and deprotecting a wide variety of functional groups are known in the art and have been reviewed in T. W. Greene, Protective Groups in Organic Synthesis, John Wiley & Sons, New York (1981). In cases wherein the spacer group is used in a protected form, an additional deprotection step may be required.

The reagents of the present invention are useful in the preparation of 5'-biotinylated oligonucleotides. Appropriate processes for using these reagents to form a covalent bond between the activatable phosphorus group, Q, and the 5'-hydroxyl group of an oligonucleotide are known. These processes can be combined with other known methods of synthesizing oligonucleotides, including those using automated DNA synthesizers, to prepare 5'-biotinylated oligonucleotides. For a general review of the field of oligonucleotide synthesis, including the phosphoramidite approach, see M. J. Gait (ed.), Oligonucleotide Synthesis, A Practical Approach, IRL Press, Oxford (1984). For a description of the use of H-phosphonate reagents in oligonucleotide synthesis, see Froehler, et al., Nucleic Acids Res. 14, 5399–5407 (1986).

EXAMPLES

General Procedure

The following Examples illustrate, but do not limit, the compounds and utilities of the present invention. Examples 1–4 demonstrate the preparation of the claimed reagents, and Examples 5 and 6 describe a process for the preparation of 5'-biotinylated oligonucleotides.

The following diagram is referred to in the Examples. Structures 3a–c and 6 are phosphoramidite reagents for the preparation of 5'-biotinylated oligonucleotides, and structures 4 and 7 are examples of 5'-biotinylated oligonucleotides that can be prepared using these reagents.

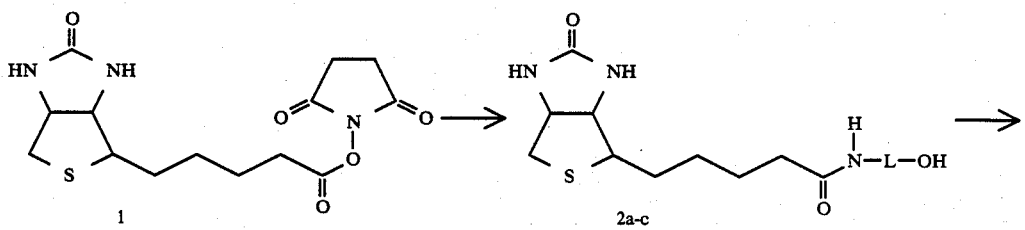

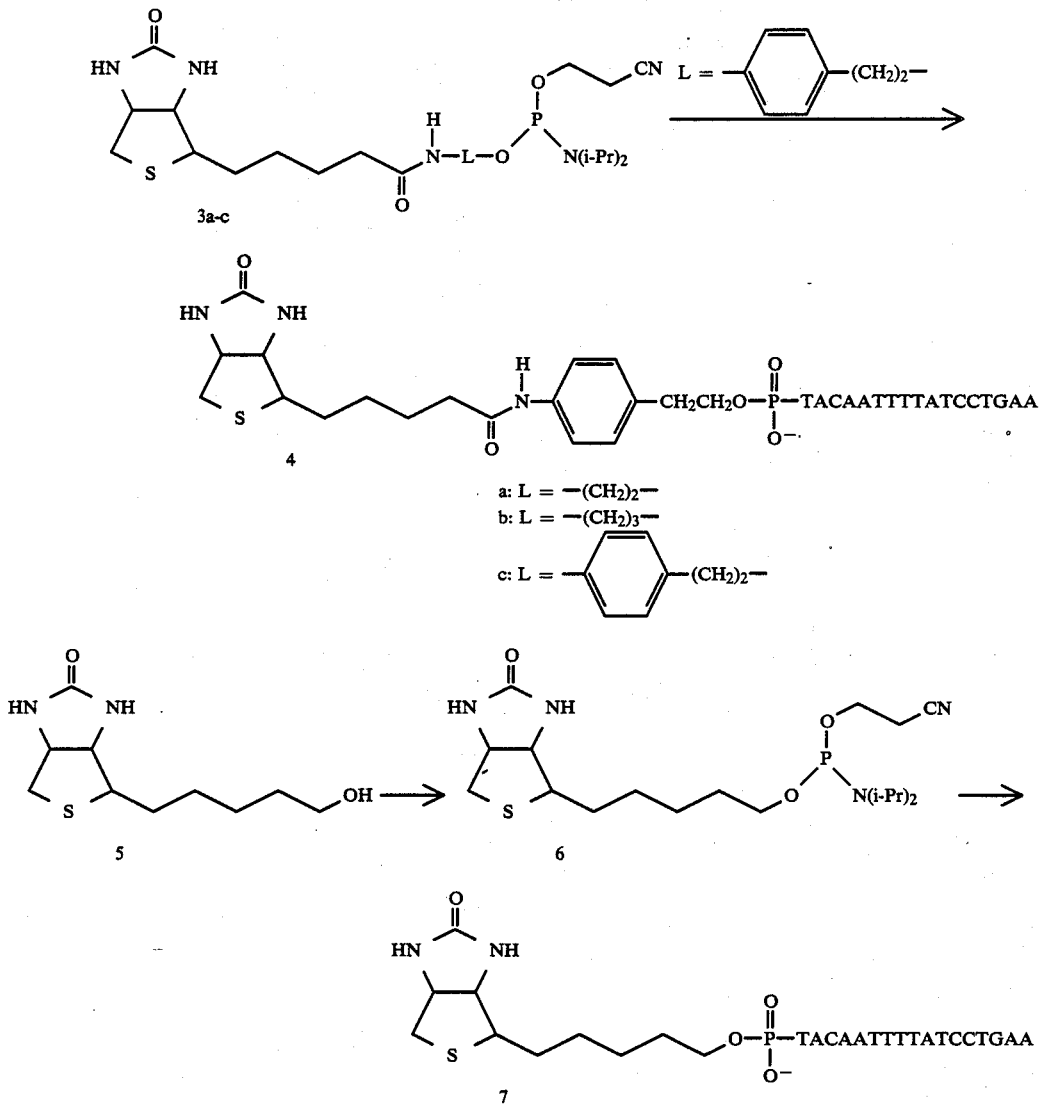

a: L = —(CH₂)₂—
b: L = —(CH₂)₃—
c: L = —C₆H₄—(CH₂)₂—

All temperatures are in degrees Celsius. The following abbreviations are employed: DMSO for dimethylsulfoxide, NMR for nuclear magnetic resonance spectrum, HPLC for high pressure liquid chromatography, and mp for melting point. In reporting NMR data, chemical shifts are given in ppm and coupling constants (J) are given in Hertz. All melting points are uncorrected. N-Hydroxysuccinimidobiotin may be purchased from Sigma Chemical Company, and 2-cyanoethyl N,N,N',N'-tetraisopropylphosphorodiamidite may be purchased from Aldrich Chemical Company.

EXAMPLE 1

Preparation of N-Biotinyl-aminoethyl 2-Cyanoethyl N,N-Diisopropylphosphoramidite 3a Step 1: Preparation of N-biotintyl-aminoethanol (2a).

To a solution of 682 mg of N-hydroxysuccinimidobiotin (1) in 12 ml of dry dimethylformamide was added 0.130 ml of ethanolamine. The resulting solution was stirred at room temperature for 30 min and then was evaporated to dryness in vacuo. The residue was recrystallized from water to afford colorless crystals that were collected by suction filtration and dried overnight in vacuo at 100° . They weighed 372 mg ( 65%), (mp 146–150°).

$^1$H-NMR (DMSO-d6): 7.71 (t, 1H, NH), 6.40 (s, 1H, NH), 6.33 (s, 1H, NH), 4.62 (s, 1H. OH). 4.27 (m, 1H, NCH), 4.10 (m, 1H, NCH), 3.31 (m, 3H, CH₂O +κH₂O ), 3.07 (m, 3H, CH₂N+SCH), 2.80 (dd, J=13, 6, 1H, SCH), 2.56 (d. J=13, 1H, SCH), 2.04 (t, J=7, 1H, CH₂CO), 1.2–1.7 (m, 6H, CH₂CH₂CH₂).

Step 2: Preparation of N-biotinyl-aminoethyl 2-cyanoethyl N,N-diisopropylphosphoramidite (3a).

To a solution of 150 mg of N-biotinylaminoethanol (2a) in 5 ml of dry DMF was added 65 mg of diisopropylammonium tetrazolide and 0.300 ml of 2-cyanoethyl N,N,N',N'-tetraisopropylphosphorodiamidite. The resulting solution was stirred at room temperature for 1.25 hr and then poured onto 50 ml of 5% aqueous sodium bicarbonate. The mixture was extracted with two 50 ml portions of methylene chloride, and the combined extracts were washed with 5% sodium bicarbonate and brine, dried over sodium sulfate, and evaporated to afford the crude product as a thick oil. This was dissolved in 2 ml of dry methylene chloride, affording a solution that was added dropwise to 30 ml of rapidly stirring petroleum ether. The colorless precipitate that formed was collected by suction filtration under argon, affording after drying at room temperature under vacuum 109 mg (43%) of a colorless solid.

$^1$H-NMR (CD$_2$Cl$_2$): 6.35 (m, 1H, NH), 6.22 (d, 1H, NH), 5.43 (m, 1H, NH), 4.47 (m, 1H, NCH), 4.30 (m, 1H, NCH), 3.5–3.9 (m, 6H, 2X CH$_2$O +2X NCH(CH$_3$)$_2$), 3.40 (m, 2H, CH$_2$N), 3.14 (m, 1H, SCH), 2.90 (dd, J=13, 6, 1H, SCH), 2.70 (d, J=13, 1H, SCH), 2.63 (t, J=7, 2H. CH$_2$CN), 2.20 (t, J=7, 2H, CH$_2$CO),1.65 (m, 4H, 2X CH$_2$), 1.43 (m, 2H, CH$_2$), 1.18 (m, 12H, 2X CH(CH$_3$)$_2$).

$^1$H-Decoupled $^{31}$P-NMR (CD$_2$Cl$_2$): 149.99 (s), 149.89 (s)(contaminants at 15.63, 10.19 and 10.01).

EXAMPLE 2

Preparation of N-Biotinyl-aminopropyl 2-Cyanoethyl N,N-Diisopropylphosphoramidite 3b Step 1: Preparation of N-biotintyl-aminopropanol (2b)

To a solution of 682 mg of N-hydroxysuccinimidobiotin (1) in 12 ml of dry dimethylformamide was added 0.160 ml of ethanolamine. The resulting solution was stirred at room temperature for 40 min and then was evaporated to dryness in vacuo. The residue was crystallized with water and then recrystallized from 15 ml of ethanol to afford colorless crystals that were collected by suction filtration and dried overnight in vacuo at 100°. They weighed 433 mg (72%), (mp 149–152°).

$^1$H-NMR (DMSO-d6): 7.70 (t, 1H, NH), 6.40 (s, 1H, NH), 6.31 (s, 1H, NH), 4.38 (s, 1H, OH). 4.25 (m, 1H, NCH), 4.08 (m, 1H, NCH), 3.33 (m, 3H, CH$_2$O +½ H$_2$O ), 3.04 (m, 3H, CH$_2$N+SCH), 2.79 (dd, J=13, 6, 1H, SCH), 2.53 (d, J=13, 1H, SCH), 2.00 (t, J=7, 2H, CH$_2$CO), 1.1–1.7 (m, 8H, 4X CH$_2$).

Step 2: Preparation of N-biotinyl-aminopropyl 2-cyanoethyl N,N-diisopropylphosphoramidite (3b).

To a solution of 150 mg of N-biotinylaminopanol (2b) in 5 ml of dry DMF was added 65 mg of diisopropylammonium tetrazolide and 0.300 ml of 2-cyanoethyl N,N,N',N'-tetraisopropylphosphorodiamidite. The resulting solution was stirred at room temperature for 1.0 hr and then poured onto 50 ml of 5% aqueous sodium bicarbonate. The mixture was extracted with two 50 ml portions of methylene chloride, and the combined extracts were washed with 5% sodium bicarbonate and brine, dried over sodium sulfate, and evaporated to afford the crude product as a thick oil. This was dissolved in 2 ml of dry methylene chloride affording a solution that was added dropwise to 30 ml of rapidly stirring petroleum ether. The colorless precipitate which formed was collected by suction filtration under argon, affording after drying at room temperature under vacuum 151 mg (60%) of a colorless solid.

$^1$H-NMR (CD$_2$Cl$_2$): 6.20 (t, 1H, NH), 6.15 (s, 1H, NH), 5.43 (s, 1H, NH), 4.48 (m, 1H, NCH), 4.28 (m, 1H, NCH), 3.4–3.9 (m, 6H, 2X CH$_2$O+2X NCH(CH$_3$)2), 3.30 (m, 2H, CH$_2$N), 3.15 (m, 1H, SCH), 2.90 (dd, J=13, 6, 1H, SCH), 2.70 (d, J=13, 1H, SCH), 2.63 (t, J=7, 2H. CH$_2$CN), 2.13 (t, J=7, 2H, CH$_2$CO), 1.78 (m, 2H, CH$_2$), 1.65 (m, 4H, 2X CH$_2$), 1.40 (m, 2H, CH$_2$), 1.15 (m, 12H, 2X CH(CH$_3$)$_2$).

$^1$H-Decoupled $^{31}$P-NMR (CD$_2$Cl$_2$): 149.31 (s) (contaminants at 122.71, 15.57, 9.95, 3.86, and 0.96).

EXAMPLE 3

Preparation of N-Biotinyl-p-aminoohenethvl 2Cyanoethl N,N-Diisopropylphosphoramidite 3c Step 1: Preparation of N-biotintyl-p-aminophenethylalcohol (2c).

To a solution of 1.60 g of N-hydroxysuccinimidobiotin (1) in 25 ml of dry dimethylformamide was added 640 mg of p-aminophenethyl alcohol. The resulting solution was stirred at 50° for 24 hr and then allowed to stand at room temperature for an additional 24 hr. The solution was evaporated to dryness in vacuo and the residue was triturated with ethanol to afford colorless crystals that were collected by suction filtration and dried overnight in vacuo at 100°. They weighed 1.05 g (62%), (mp 200°–203°).

$^1$H-NMR (DMSO-d6): 9.80 (s, 1H, NH), 7.50 (d, J=10, 2H, ArH), 7.10 (d, J=10, 2H, ArH), 6.45 (s, 1H, NH), 6.40 (s, 1H, NH), 4.65 (s, 1H, OH). 4.32 (m, 1H, NCH), 4.15 (m, 1H, NCH), 3.55 (m, 2H, CH$_2$O), 3.(m, 2H, SCH), 2.83 (dd, J=13, 6, 1H, SCH), 2.65 (t, J=7, 2H, CH$_2$Ph), 2.60 (d. J=13, 1 1H, SCH), 2.30 (t, J=7, 1H, CH$_2$CO), 1.2–1.7 (m, 6H, CH$_2$CH$_2$CH$_2$).

Step 2: Preparation of N-biotinyl-p-aminophenethyl 2-cyanoethyl N,N-diisopropylphosphoramidite (3c).

To a solution of 150 mg of N-biotintyl-p-aminophenethylalcohol in 5 ml of dry DMF was added 35 mg of diisopropylammonium tetrazolide and 0.175 ml of 2-cyanoethyl N,N,N',N'-tetraisopropylphosphorodiamidite. The resulting solution was stirred at room temperature for 2.25 hr and then poured onto 50 ml of 5% aqueous sodium bicarbonate. The mixture was extracted with two 25 ml portions of methylene chloride, and the combined extracts were washed with 5% sodium bicarbonate and brine, dried over sodium sulfate, and evaporated to afford 247 mg of crude product as a thick oil. This was dissolved in 2 ml of dry methylene chloride affording a solution that was added dropwise to 30 ml of rapidly stirring petroleum ether. The colorless precipitate that formed was collected by suction filtration under argon affording after drying at room temperature under vacuum 149 mg (64%) of a free-flowing powder.

$^1$H-NMR (CD$_2$Cl$_2$): 8.30 (m, 1H, NH), 7.50 (d, J=7, 2H, ArH), 7.15 (d, J=7, 2H. ArH), 6.55 (d, 1H, NH), 5.52 (m, 1H, NH), 4.47 (m, 1H, NCH), 4.30 (m, 1H, NCH), 3.5–3.9 (m, 6H, 2X CH$_2$O+2X NCH(CH$_3$)$_2$), 3.14 (m, 1H, SCH), 2.80–2.95 (m, 3H, CH$_2$Ph +SCH) 2.65 (d, J=13, 1H, SCH), 2.57 (t, J=7, 2H, CH$_2$CN), 2.30 (t, J=7, 1H, CH$_2$CO), 1.75 (m, 4H, 2X CH$_2$), 1.43 (m, 2H, CH$_2$), 1.15(m, 12H, 2X CH(CH$_3$)$_2$).

$^1$H-Decoupled $^{31}$P-NMR (CD$_2$Cl$_2$): 148.96 (s) (contaminants at 15.57, 14.82, 9.09, 3.33, and 7.34).

EXAMPLE 4

Preparation of Biotinoxy 2-Cyanoethoxy bis-Diisopropylamino Phosphine 6

To a solution of 443 mg of biotinol (5) in 20 ml of dry methylene chloride was added 190 mg of diisopropylammonium tetrazolide and 0.900 ml of 2-cyanoethyl N,N,N',N'-tetraisopropylphosphorodiamidite. The resulting mixture was stirred at room temperature for 1 hr and then poured onto 100 ml of 5% aqueous sodium bicarbonate. The mixture was extracted with 100 ml of methylene chloride, and the extract was washed with 5% sodium bicarbonate and brine, dried over sodium sulfate, and evaporated to afford 885 mg of crude product. This was dissolved in 3 ml of dry methylene chloride affording a solution that was added dropwise to 30 ml of petroleum ether. The colorless precipitate that formed was collected by centrifugation affording after drying under vacuum at room temperature 427 mg (52%) of a slightly gummy colorless solid.

$^1$H-NMR (CD$_2$Cl$_2$): 5.33 (t, 1H, NH), 5.27 (s, 1H, NH), 4.48 (m, 1H, NCH), 4.28 (m, 1H, NCH), 3.4–3.9 (m, 6H, 2X CH$_2$O+2X NCH(CH$_3$)$_2$), 3.15 (m, 1H, SCH), 2.90 (dd, J=12, 5, 1H, SCH), 2.68 (d, J=12, 1H, SCH), 2.62 (t, J=7, 2H. CH$_2$CN), 2.13 (t, J=7, 2H, CH$_2$CO), 1.62 (m, 4H, 2X CH$_2$), 1.40 (m, 4H, 2X CH$_2$), 1.15 (m, 12H, 2X CH(CH$_3$)$_2$). $^1$H-Decoupled $^{31}$P-NMR (CD$_2$Cl$_2$): 148.90 (s) (contaminants at 15.59 and 9.42).

EXAMPLE 5

Preparation of N-Biotinyl-p-aminophenethoxy-pTACAATTT-TATCCTGAA 4, An Oligonucleotide with Biotin Attached to the 5′-Phosphate Through a p-Aminophenethanol Linker Automated oligonucleotide synthesis was performed on a Du Pont Coder ® 300, according to the general methods described in the operator's manual. The sequence "5′ XTACAATTTTATCCTGAA 3′" was entered and the following options were selected: (1) Use capping step? YES. (2) Remove 5′ terminal DMT? NO. (3) Collect DMT? YES. (4) Synthesis scale 1 μmole. The instrument was charged with reagents supplied commercially by Du Pont and an 0.15 M solution of phosphoramidite 3c in dry methylene chloride was placed on the "X" port. The starting material in the synthesis column was protected 2′-deoxyadenosine (1 μmol) on long chain alkylamine controlled pore glass. Automated synthesis was run without any modification during or after the use of phosphoramidite 3c. After automated synthesis was complete, the solid supported oligonucleotide was treated with concentrated ammonia, as described in the Coder 300 ® operator's manual to deprotect the oligonucleotide and remove it from the solid support. The ammonia solution was concentrated under vacuum to afford the crude product.

Analysis of the crude product by HPLC (25 cm 300A° C$_8$ reverse phase column eluted for 32 minutes with a gradient of 5–15% acetonitrile in 0.1 M aqueous triethylammonium acetate) with detection at 260 nm showed only one significant product with a retention time of 27.9 min. The crude product was purified by preparative HPLC using the same conditions used for the analytical HPLC. The yield of the purified oligonucleotide was, as assayed by UV, 8.8 ODU (260 nm) or approximately 49 nanomoles. The product was lyophilized, dissolved in sterile distilled water, and stored frozen at −25° until used.

It was demonstrated that biotin was attached to the oligonucleotide and that it was available for binding to streptavidin by the ability of streptavidin-coated magnetic beads to remove biotinylated oligonucleotide 4 from aqueous solution relative to a nonbiotinylated oligonucleotide. Both 4 and a reference nonbiotinylated oligonucleotide were 3′-labeled with a fluorescent tag by the method of Trainor, et al., Nucleic Acids Res. 16, 11846 (1988). An aqueous solution of a mixture of fluorescence-labeled 4 and fluorescence-labeled reference oligonucleotide was treated with streptavidin coated magnetic beads for 30 min at 37°. The suspended beads were coagulated into a pellet with a magnet, and the supernatant was drawn off and analyzed for the presence of the two fluorescence labeled oligonucleotides by polyacrylamide gel electrophoresis (12% gel) with a Du Pont Genesis ® 2000 DNA sequencer.

This analysis revealed that 97% of 4 was removed from solution relative to the reference oligonucleotide.

EXAMPLE 6

Preparation of Biotinoxy-pTACAATTTTTCCTGAA 7, An Oligonucleotide with Biotinol Attached to the 5′-Phosohate Automated oligonucleotide synthesis was performed on a Du Pont Coder ® 300 using essentially the same procedure described in Example 5, with the exception that a 0.2 M solution of phosphoramidite 6 in dry methylene chloride was placed on the "X" port. The crude product (retention time of 22.0 min) was purified by HPLC, and the yield of purified oligonucleotide was 17.9 ODU or approximately 100 nanomoles.

A similar analysis to that described in Example 5 revealed that 98% of 7 could be removed from aqueous solution with streptavidin-coated magnetic beads.

What is claimed is:

1. A chemical compound of the formula
   Bt-(SG)-A-Q wherein
Bt is

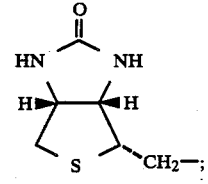

SG is an organic diradical spacer group that separates Bt from A at a distance sufficient to allow efficient complexation of Bt to avidin or streptavidin;
A is selected from the group consisting of —O—, —S—,

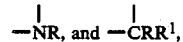

wherein R and R$^1$ are independently selected from the group consisting of H, C$_{3-10}$ branched alkyl, C$_{1-10}$ unbranched alkyl, C$_{6-10}$ *aryl*, C7-12 *alkaryl, and C7-12 aralkyl*;
Q is selected from the group consisting of

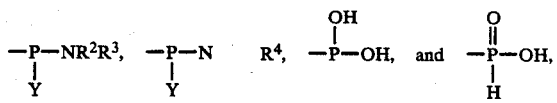

and salts thereof; wherein R$^2$ and R$^3$ are independently selected from the group consisting of C$_{3-10}$ branched alkyl and C$_{1-12}$ unbranched alkyl; R$^4$ is selected from the group consisting of —(CRR$^1$)-$_m$(A)$_n$(CRR$^1$)m—,

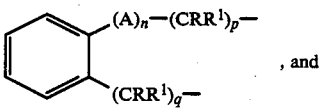

, and

-continued

R, R$^1$ and A are as defined above; m=1-6; n=0-1; p=1-10; q=0-10, provided that 2m+n≦12, and further provided that 2≦n+p+q≦13; and Y is any phosphate-protecting group.

2. A compound according to claim 1 wherein SG is —(CH$_2$)$_r$—X—; r=2-3; X is selected from the group consisting of —CH$_2$—, —X$^1$L—, and

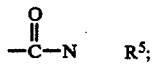

X$^1$ is selected from the group consisting of —CH$_2$O—, —CH$_2$S—,

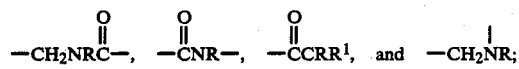

R and R$^1$ are as defined above; and R$^5$ is selected from the group consisting of

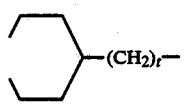

and alkyl-substituted derivatives thereof; t=0-10; and L is selected from the group consisting of substituted and unsubstituted derivatives selected from the group consisting of C$_{2-20}$ alkylene wherein the alkylene segment may contain one or more groups selected from the group consisting of arylene, cycloalkylene, heterocyclene, ether, thioether, sulfone, sulfoxide, amide, ureido, keto, and dithio; C$_{3-8}$ *cycloalkylene; C$_{4-20}$. alkylenecycloalkyl; C$_{6-10}$ arylene;*

wherein z=1-10; C$_{7-20}$ *arylalkylene; and* 3-10 membered ring aromatic or alicyclic heterocyclenes wherein the heteroatom(s) may be selected from the group Consisting of N, O, and S.

3. A compound according to claim 2 wherein r is 2, X is —CH$_2$—, and A is —CH$_2$—.

4. A compound according to claim 2 wherein r is 3.

5. A compound according to claim 4 wherein X is —CH$_2$—.

6. A compound according to claim 4 wherein A is —O—.

7. A compound according to claim 6 wherein X is —CH$_2$—.

8. A compound according to claim 6 wherein X is

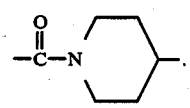

9. A compound according to claim 6 wherein X is —X$^1$—L—, X$^1$ is

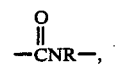

and R is selected from the group consisting of H, C$_{1-4}$ unbranched alkyl, and C$_{3-5}$ branched alkyl.

10. A compound according to claim 9 wherein R is selected from the group consisting of H and CH$_3$.

11. A compound according to claims 3, 5, 7, 8, or 10 wherein Q is selected from the group consisting of

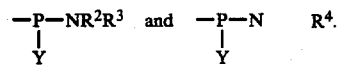

12. A compound according to claim 11 wherein Y is selected from the group consisting of 4—Cl—C$_6$H$_4$—O—; 2—Cl—C$_6$H$_4$—O—; 4—NO$_2$—C$_6$H$_4$—O—; 4—NO$_2$—C$_6$H$_4$CH$_2$CH$_2$l —O—; 2,4—NO$_2$—C$_6$H$_3$CH$_2$CH$_2$—O—; 2,4-Cl$_2$—C$_6$H$_3$—O—; 2,3-Cl$_2$—C$_6$H$_3$—O—; NCCH$_2$CH$_2$O—; NCCH$_2$C(CH$_3$)$_2$—O—; CH$_3$O—; (Z)$_3$CCH$_2$—O—; (Z)$_3$CC(CH$_3$)$_2$—O—R'S—; R'SCH$_2$CH$_2$—O—; R'SO$_2$CH$_2$CH$_2$—O—; and R'NH—, wherein Z is selected from the group consisting of Cl, Br, and I, and R' is selected from the group consisting of H, C$_{3-1}$ branched alkyl, C$_{1-10}$ unbranched alkyl, C$_{6-10}$ aryl, C$_{7-12}$ alkaryl, and C$_{7-12}$ aralkyl.

13. A compound according to claim 12 wherein Q is

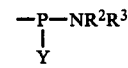

and R$^2$ and R$^3$ are —CH(CH$_3$)$_2$.

14. A compound according to claim 13 wherein Y is selected from the group consisting of NCCH$_2$CH$_2$O— and CH$_3$O—.

15. A compound according to claim 14 wherein R is H and L is C$_{2-20}$ alkylene.

16. A compound according to claim 15 wherein L is selected from the group consisting of —(CH$_2$)$_2$— and —(CH$_2$)$_3$—.

17. A compound according to claim 14 wherein R is H and L is 1,4-cyclohexylene.

18. A compound according to claim 14 wherein R is H, L is

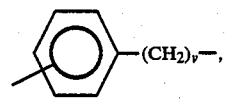

and v=1-10.

19. A compound according to claim 18 wherein L is

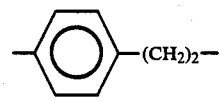

20. A compound according to claim 14 wherein

R is H, L is
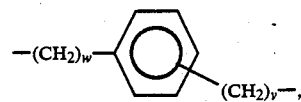
v is 1–10 and w is 1–10.
* * * * *